United States Patent [19]
Langer et al.

[11] Patent Number: 6,043,394
[45] Date of Patent: Mar. 28, 2000

[54] PROCESS FOR PRODUCING AROMATIC AMINES BY GASEOUS PHASE HYDROGENATION

[75] Inventors: Reinhard Langer; Hans-Josef Buysch; Manfred Gallus, all of Krefeld; Burkhard Lachmann, Meerbusch; Franz-Ulrich von Gehlen, Krefeld, all of Germany

[73] Assignee: Bayer Aktiengesellschaft, Leverkusen, Germany

[21] Appl. No.: 09/319,486

[22] PCT Filed: Dec. 1, 1997

[86] PCT No.: PCT/EP97/06730

§ 371 Date: Jun. 4, 1999

§ 102(e) Date: Jun. 4, 1999

[87] PCT Pub. No.: WO98/25881

PCT Pub. Date: Jun. 18, 1998

[30] Foreign Application Priority Data

Dec. 12, 1996 [DE] Germany ............................ 196 51 688

[51] Int. Cl.[7] .................................................. C07C 209/00
[52] U.S. Cl. ........................................... 564/423; 564/422
[58] Field of Search ...................................... 564/422, 423

[56] References Cited

U.S. PATENT DOCUMENTS

| | | |
|---|---|---|
| 3,882,048 | 5/1975 | Thelen et al. . |
| 4,265,834 | 5/1981 | Birkenstock et al. . |
| 5,304,525 | 4/1994 | Immel et al. . |

FOREIGN PATENT DOCUMENTS

| | | |
|---|---|---|
| 2525591 | 10/1983 | France . |
| 2135155 | 2/1973 | Germany . |

*Primary Examiner*—Paul J. Killos
*Attorney, Agent, or Firm*—Joseph C. Gil; Diderico van Eyl

[57] ABSTRACT

A process for the production of aromatic amines by catalytic hydrogenation.

4 Claims, No Drawings

PROCESS FOR PRODUCING AROMATIC AMINES BY GASEOUS PHASE HYDROGENATION

FIELD OF THE INVENTION

Process for the production of aromatic amines by gas phase hydrogenation The present invention relates to a process for the production of aromatic amines by catalytic hydrogenation of corresponding aromatic nitro compounds in the gas phase on inunobilised supported catalysts.

BACKGROUND OF THE INVENTION

It is known to hydrogenate nitrobenzene and other nitroaromatics to yield the corresponding aromatic amines in the gas phase on immobilised supported catalysts. FR 25 25 591, for example, thus describes a process for hydrogenating nitrobenzene on stationary copper catalysts. DE-A 2 135 155 and 2 244 401 futhermore describe processes for reducing nitro compounds in the presence of supported catalysts containing palladium using spinels as the support materials. DE-A 2 849 002 also describes a process for the catalytic hydrogenation of nitrobenzene, in which hydrogenation is performed in the presence of a multi-component supported catalyst. A disadvantageous feature of the gas phase hydrogenations described in the stated patent publications is the low loading (specific loading) of the catalysts. The stated or calculated loadings vary between 0.2 and 0.6 kg/l×h. Loading is here defined as the quantity of nitroaromatics in kg which are reacted per litre of catalyst bed within one hour. The low catalyst loading is accompanied by an unsatisfactory space/time yield in large scale industrial processes for the production of aromatic amines.

DE-A 4 039 026 describes a gas phase hydrogenation on palladium catalysts which may be highly loaded. Catalyst loading in this process is between 0.6 and 0.95 kg/l×h. Industrial performance of the process has, however, revealed that after only a short time conversion of the nitrobenzene proceeds only incompletely, such that the condensate contains not inconsiderable quantities of unreacted nitrobenzene in addition to the aromatic amine which has been formed. If the nitrobenzene content is to be reduced to below the tolerable limit, the aniline must be purified by elaborate purification methods (distillation). It has furthermore been found that, at the high catalyst loading, the catalysts used in DE-A 4 039 026 have only an unsatisfactory service life.

The object of the present invention was to provide a process for the production of aromatic amines by catalytic hydrogenation of the corresponding nitro compounds in the gas phase, which may be performed without problems on an industrial scale and which ensures an elevated space/time yield, combined with improved productivity of the catalysts used.

This objective is achieved with the process according to the invention.

SUMMARY OF THE INVENTION

The present invention accordingly provides a process for the production of aromatic amines by catalytic hydrogenation of corresponding aromatic nitro compounds in the gas phase on immobilised catalysts which contain one or more metals of groups VIIIa, Ib, IIb, IVa, Va, VIa, IVb and Vb of the periodic system of elements (Mendeleyev) on a ceramic support material having a BET surface area of less than 40 m$^2$/g, at molar ratios of hydrogen to nitro group or nitro groups of 3:1 to 30:1 and temperatures in the catalyst bed of 180 to 500° C., which process is characterised in that loading of the catalyst with the aromatic nitro compounds used is increased continuously or step-wise from 0.01–0.5 to 0.7–5.0 kg/l×h, wherein maximum loading is achieved within 10 to 1000 hours.

DESCRIPTION OF THE INVENTION

Aromatic nitro compounds which may be used in the process according to the invention are those of the following formula

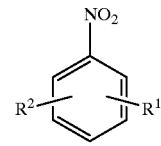

in which

R$^1$ and R$^2$ are identical or different and denote C$_1$–C$_4$ alkyl, in particular methyl and ethyl, hydrogen or the nitro group.

Nitrobenzene or the isomeric nitrotoluenes, in particular nitrobenzene, are used in the hydrogenation process according to the invention.

Catalysts suitable for the process according to the invention are any known for the hydrogenation of nitro groups and in which the metals of the above-mentioned main and sub-groups of the periodic system of elements have been applied onto a ceramic support. The metals may have been applied onto the catalyst support in elemental form or in the form of a compound. Metals which may be applied onto a ceramic support which may in particular be mentioned are Fe, Co, Pd, Pt, Cu, Ag, Zn, Ti, Zr, Hf, V, Nb, Ta, Cr, Mo, W, Ge, Sn, Pb, As, Sb, Bi, particularly preferably Fe, Pd, Pt, Cu, Ti, V, Nb, Cr, Mo, Sn, Pb, Sb, Bi, very particularly preferably Pd, V, Pb, Bi. The metals may have been applied onto the ceramic support individually or as a mixture with each other.

Suitable ceramic support materials for the stated metals are in principle any ceramic solids having BET surface areas of less than 40 m$^2$/g, preferably of less than 20 m$^2$/g, in particular of less than 10 m$^2$/g. Suitable ceramic solids are in particular metal oxides and/or metal mixed oxides of the elements magnesium, aluminium, silicon. germanium, zirconium and titanium, with a-aluminium oxide being preferably used as the support material.

Catalysts as are described in DE-A 2 849 002 have proved to be particularly suitable. Catalysts which may in particular be mentioned are those containing primarily palladium, vanadium and lead among other metals deposited as a shell on a-aluminium oxide. Particular emphasis should thus be placed on catalysts which contain a) 1 to 50 g of palladium, b) 1 to 50 g of titanium, vanadium, niobium, tantalum, chromiun, molybdenum and/or tungsten and c) 1 to 20 g of lead and/or bismuth per litre of oxide support material, wherein the support material has a surface area of less than 40, preferably of less than 20, in particular of less than 10 m$^2$/g. Of the stated metals in the mixed catalyst, palladium, vanadium and lead in the above-stated quantities have again proved particularly favourable in use.

Production of the catalysts is known from the cited patent literature. It has been found to be advantageous if the active component of the catalyst is deposited as a well defined zone as close as possible to the surface of the moulded catalyst shape and the interior of the support material contains no metal. The catalysts may here be produced with or without pretreatment of the support material with a base.

In principle, the supported catalysts for the process according to the invention may have any desired shape, such as spheres, rods, Raschig rings, pellets or tablets. The moulded shapes used are preferably those which, as beds, exhibit low flow resistance with good gas surface contact, such as Raschig rings, saddles, waggon wheels and/or spirals. It is possible in the process according to the invention for the catalyst bed in the reactors to consist solely of the supported catalyst or for it to be additionally diluted with inert support material or other inert packing, such as for example glass or ceramic. The catalyst bed may consist of up to 90 wt. %, preferably up to 75 wt. %, in particular up to 50 wt. % of inert packing or support material. The bed may have a dilution gradient such that dilution decreases in the direction of flow. At the feed surface, the bed may contain between 10 to 50 wt. % of packing material and, at the outlet end, consist of 80 to 100 wt. % of pure supported catalyst.

Reactors which may be used for the process according to the invention are any known reactors which are suitable for gas phase reactions with cooled, stationary catalyst beds. Suitable reactors are, for example, multi-tube reactors in which the catalyst is located within tubes around which a heat transfer medium flows and reactors in which, conversely, the heat transfer medium flows within the tubes and the catalyst is located outside the tubes. Such reactors are known, for example, from DE-A 2 848 014 and 3 007 202.

Reactors which have proved to be particularly advantageous for the process according to the invention are those in which the heat transfer medium flours within the tubes and the catalyst is located outside the tubes (Linde type reactors). In comparison with conventional multi-tube reactors, constant operating times between regenerations are observed over many regeneration cycles in these reactors.

The length of the catalyst bed in the direction of flow in the process according to the invention is from 0.5 to 20, preferably from 1 to 10, more preferably from 2 to 6 m.

The process according to the invention is preferably performed at molar ratios of hydrogen to nitro group or nitro groups of the nitro compound used of 4:1 to 20:1, preferably from 5:1 to 10:1.

Hydrogen concentration may be reduced by incorporating inert carrier gases, such as nitrogen, helium, argon and/or steam. Nitrogen is preferably used. Up to 10 mol, preferably up to 3 mol, more preferably up to 1 mol of inert carrier gas may be introduced per mol of hydrogen.

Dilution with inert carrier gas is preferably used at the beginning of the period of operation with fresh catalyst and after regeneration of the catalyst by burning off with air and reduction with hydrogen. Dilution with inert gas is preferably performed for the first 300 hours, more preferably for the first 200 hours, most preferably for the first 100 hours after starting up again with inert gas.

Deactivated beds are regenerated with $N_2/O_2$ mixtures at temperatures of between 200 and 400° C., preferably between 250 and 350° C. on the solid catalyst, with regeneration preferably being begun at $N_2$ contents of between 90 and 99% in the gas stream and the $O_2$ content being raised in stages to pure air during burning off, and, at the end of regeneration, tenacious carbon residues may optionally be burnt off with pure oxygen. Inert carrier gases other than nitrogen, such as for example argon, helium or steam, may also be added to oxygen or air.

The process according to the invention is preferably performed at temperatures within the range from 180 to 500, more preferably from 200 to 460, most preferably 220 to 440° C. It may be advantageous in this connection if the temperature of the cooling medium in the process according to the invention is raised continuously or step-wise during the operating cycle.

The process according to the invention is operated at a pressure of 0.5 to 5, preferably of 1 to 3 bar.

An essential feature of the process according to the invention is that loading of the catalyst with the aromatic nitro compounds used is raised continuously or step-wise to the desired loading value within a certain period of time. A mode of operation is accordingly preferred in which catalyst loading is raised continuously or step-wise within 20 to 500, more preferably within 30 to 300, most preferably within 40 to 200 hours, and from 0.01–0.5, preferably from 0.1–0.4, more preferably from 0.15–0.3 to 0.7–5.0, preferably to 0.8–3.0, more preferably to 1.0–2.0 kg/l×h.

The elevated final loading is maintained until unreacted educt breaks through. Once the educt concentration becomes excessively high at the end of the reactor, the temperature of the heat transfer medium may be raised and/or educt loading reduced, in order to delay an interruption in production for catalyst regeneration.

In a particular embodiment of the process according to the invention, beds are used in which the supported catalysts described above are used mixed with another solid catalyst, in which palladium has been applied onto graphite or coke containing graphite as the support material and in which the support material has a BET surface area of 0.05 to 10 $m^2/g$, preferably of 0.2 to 5 $m^2/g$. The palladium content of the graphite-supported catalyst is 0.1 to 7 wt. %, preferably 1.0 to 6 wt. %, more preferably 1.5 to 5 wt. %, most preferably 2 to 4 wt. %. The stated supported palladium catalysts containing graphite are described, for example, in DE-A 2 849 002.

If the supported catalysts based on a ceramic support material and the supported catalysts based on graphite as the support material are used as mixtures with each other, the ratio of weights in the mixture is 1/1 to 1000/l, preferably 10/1 to 100/l, more preferably 90/1 to 99/1 (ceramic supported catalyst to graphite supported catalyst).

The graphite catalyst is preferably used in the first third of the catalyst bed, but may also be distributed uniformly throughout the entire bed.

The process according to the invention may, for example, be realised industrially in the following manner: a circulating gas stream substantially consisting of hydrogen and a little water is compressed in order to overcome the plant's resistance to flow. The gas stream is heated by countercurrent heat exchange, wherein the heat is taken, for example, from the circulating gas stream before condensation of the products. The circulating gas stream is adjusted to the desired temperature. The nitroaromatic compound to be hydrogenated is vaporised and superheated in fresh hydrogen, which replaces that consumed, and the two gas streams are then mixed. The gas mixture is introduced into a temperature-controlled reactor with stationarily arranged catalyst. The liberated heat of reaction is removed from the reactor by means of a heat transfer medium. The product stream leaving the reactor is used to heat the circulating gas stream and then cooled with water until the aniline formed condenses. The liquids are discharged, together with a small quantity of circulating gas in order to remove gases, for example nitrogen, which would otherwise accumulate. The circulating gas is then returned to the compressor.

In a preferred embodiment of the process according to the invention, the catalyst bed is introduced into a Linde type reactor (heat transfer medium flows within the reactor tubes and the catalyst is arranged outside the heat transfer medium tubes) and the process is performed as described above. To this end, fresh or freshly regenerated catalyst is operated with nitrogen/hydrogen mixtures for the first hours. The advantages of this preferred mode of operation are: elevated selectivity and long periods of time between regenerations, even after many production cycles.

The process according to the invention is in particular distinguished by the elevated space/time yields which may be achieved, combined with a reduction in size of the necessary plant and equipment and distinctly increased catalyst productivity. Considerable increases in output may thus be achieved in existing plant by means of the process according to the invention.

A particularly favourable development of the process according to the invention is that in which supported catalysts having ceramic support materials are used in combination with supported catalysts having a graphite support, using a reactor type in which the supported catalysts are located outside the tubes containing the heat transfer oil (Linde type).

The invention is further illustrated in the following examples. All references to parts and percentages are by weight unless otherwise indicated.

EXAMPLES

Catalyst Preparation on a Ceramic Support.

Example 1

One litre of an a-$Al_2O_3$ support in spherical form having a diameter of 3 to 5 nmm, a BET surface area of 9.8 $m^2$/g, an absorption capacity of 45.1 ml of water per 100 g of support and a bulk density of 812 g/l was impregnated with 366 ml of an aqueous solution containing 10.8 g (corresponding to 0.27 gram-equivalents) of NaOH. The solution was completely absorbed by the support within a few minutes.

The moist support was dried in a warm, increasingly strong stream of air. Drying time to constant weight was approx. 15 minutes. After cooling, the residual moisture content was approx. 1% of the absorption capacity of the support.

The dry support pretreated in this manner was saturated in accordance with its absorption capacity with 366 ml of an aqueous sodium tetrachloropalladate solution which contained 9 g of palladium (corresponding to 0.169 gram-equivalents) and left to stand for 15 minutes. In order to reduce the palladium compound which had been deposited on the support to metallic palladium, the catalyst was covered with 400 ml of a 10% aqueous hydrazine hydrate solution and left to stand for 2 hours. The catalyst was then thoroughly rinsed with completely deionised water until no ions of the compounds used in catalyst production were any longer detectable in the rinsing water, which took some 10 hours.

Drying to constant weight was then again performed in a strong, increasingly warm stream of air.

The catalyst containing Pd was then saturated with 366 ml of an aqueous solution containing 9 g of vanadium as vanadyl oxalate. The support was dried in a stream of warm air as described above. The catalyst was then heat treated for 6 hours at 300° C. in a tubular oven, wherein the oxalate was decomposed.

The catalyst was then saturated with 366 ml of an aqueous solution containing 3 g of lead as lead acetate and again dried in the increasing air stream.

The completed catalyst contained 9 g of Pd, 9 g of vanadium and 3 g of lead and matched the catalyst from Example 1 in DE-OS 2849002.

Examples with Catalyst Beds Containing Ceramic Supported Catalysts

Example 2 (Comparative Example 1)

A 285 cm deep bed of a catalyst produced according to Example 1 was charged into a reaction tube of an internal diameter of approx. 26 mm and temperature-controlled with oil. The catalyst was flushed first with nitrogen, then with hydrogen and then heated within 5 hours to 240° C. in a stream of hydrogen of approx. 770 Nl/h. Vaporisation of nitrobenzene in the stream of hydrogen was then begun. The nitrobenzene/hydrogen mixture arrived at the face of the catalyst bed at approx. 230° C. The specific loading of the catalyst was increased within 48 hours from 0.1 to 0.47 kg/l×h, corresponding to a loading per unit area of 1425 kg/$m^2$×h, such that a mean loading of 0.46 kg/l×h was achieved. The temperature in the entire bed was monitored throughout the test and it was ensured that the catalyst temperature did not exceed 440° C. at any point.

The oil temperature was raised in 20° C. stages after approx. 700, 800 and 900 hours from 240° C. to 300° C. The variation in oil temperature along the reaction tube was approx. ±1° C. The flow velocity of the oil along the tube surface was approx. 1.5 m/s.

The catalyst achieved a service life of approx. 1450 hours, after which the nitrobenzene content of the condensate rose from 0 to approx. 300 ppm. Thereupon, the catalyst had to be regenerated by burning off. Under the stated reaction conditions, the catalyst thus achieved a productivity of approx. 670 kg/l. Mean selectivity was 98.4%.

The catalyst behaved identically in the second cycle after regeneration, giving a service life of 1400 hours and 98.6% selectivity.

Example 3

A 285 cm deep bed of a catalyst produced according to Example 1 was charged into a reaction tube of an internal diameter of approx. 26 mm and temperature-controlled with oil. The catalyst was flushed first with nitrogen, then with hydrogen and then heated within 5 hours to 240° C. in a stream of hydrogen of approx. 1528 Nl/h. Vaporisation of nitrobenzene in the stream of hydrogen was then begun. The nitrobenzene/hydrogen mixture arrived at the face of the catalyst bed at approx. 230° C. The specific loading of the catalyst was increased within 80 hours from 0.2 to 1.05 kg/l×h, corresponding to a loading per unit area of 2994 kg/$m^2$×h, such that a mean loading of 1.03 kg/l×h was achieved. It was ensured that the catalyst did not become hotter than 440° C. at any point throughout the test.

The oil temperature was raised in 20° C. stages after approx. 700, 800 and 900 hours from 240° C. to 300° C. The variation in oil temperature along the reaction tube was approx. ±1° C. The flow velocity of the oil along the tube surface was approx. 1.5 m/s.

The catalyst achieved a service life of approx. 1050 hours, after which the nitrobenzene content of the condensate rose from 0 to approx. 300 ppm, whereupon the catalyst had to be regenerated by burning off. Under the stated reaction conditions, the catalyst thus achieved a productivity of approx. 1080 kg/l, approx. 1.6 times as productive as in the Comparative Example.

Mean selectivity was 99.0%, 0.6% higher than that of the Comparative test.

The catalyst behaved identically in the second cycle after regeneration, giving a service life of 990 hours and 99.2% selectivity.

Since the catalyst regeneration time of a few hours is not of great significance in comparison with the cycle time, the quantity of aniline produced per unit time is twice as high as in the Comparative Example due to the elevated loading. Catalyst preparation on a graphite support.

The support material used comprised EG 17 graphite pellets supplied by Ringsdorff having a BET surface area of approx. 0.4–0.8 $m^2/g$. Grain size was between 4 and 5 mm.

The Examples should not in any way be viewed as restrictive: similar results are also achieved with other graphites and materials containing graphite having a low BET surface area.

The catalysts are prepared in the following manner: EG 17 graphite pellets supplied by Ringsdorff (4–5 mm pellets, shaken density 650–1000 g/ml) having an absorption capacity of 7 ml of acetonitrile per 10 g of support are introduced into a rotatable vessel and combined, while the vessel is rotated, with a solution of palladium acetate in acetonitrile. The mixture is kept in motion until the solution has been completely absorbed. The solid is then dried for 5 minutes in a increasingly strong stream of warm air at 40° C. The saturation and drying stages are repeated until the desired quantity of palladium has been deposited.

The dried catalyst is then activated in a hot stream of hydrogen at standard pressure.

Example 4

0.6% Pd on EG17

2000 g of support 3 saturation stages, each comprising 8.3 g of $PdAc_2$ in 140 g of acetonitrile, activated for 20 h at 370° C. in a stream of $H_2$.

Example 5

2.4% Pd on EG17

2000 g of support 10 saturation stages, each comprising 10 g of $PdA_c$ in 140 g of acetonitrile, activated for 20 h at 370° C. in a stream of $H_2$.

Example With Catalyst Bed Containing Graphite Supported Catalyst and Inert Supports.

Example 6 (Comparative Example 2)

A 285 cm deep bed of a catalyst produced according to Example 4 was charged into a reaction tube of an internal diameter of approx. 26 mm and temperature-controlled with oil. The catalyst bed was sub-divided into six sections approx. 47.5 cm in length, in which the catalyst was packed homogeneously diluted with untreated support material. Dilution decreased in the direction of flow as follows: 97%, 94%, 88%, 60%, 60%, 0%. The final section thus contained undiluted catalyst.

The bed was flushed first with nitrogen, then with hydrogen and then heated within 5 hours to 240° C. in a stream of hydrogen of approx. 1528 Nl/h. Vaporisation of nitrobenzene in the stream of hydrogen was then begun. The nitrobenzene/hydrogen mixture arrived at the face of the catalyst bed at approx. 230° C. The specific loading of the catalyst was increased within 60 hours from 0.4 to 0.84 kg/l×h, corresponding to a loading per unit area of 2395 kg/$m^2$×h. It was ensured that the catalyst did not become hotter than 440° C. at any point throughout the test.

The variation in oil temperature along the reaction tube was approx. ±1° C. The flow velocity of the oil along the tube surface was approx. 1.5 m/s.

The catalyst achieved a service life of approx. 70 hours, after which the nitrobenzene content of the condensate rose from 0 to approx. 300 ppm. Under the stated reaction conditions, the catalyst had thus achieved a productivity of approx. 50 kg/l. Mean selectivity was 99.5%.

Raising the temperature of the heat transfer medium from 240 to 260 and 300° C. did not counteract break-through of the nitrobenzene, which rapidly rose to more than 10%.

Examples with Catalyst Beds Containing both Ceramic and Graphite Supported Catalysts.

Example 7

A 285 cm deep bed of catalysts produced according to Examples 4 and 1 was charged into a reaction tube of an internal diameter of approx. 26 nmu and temperature-controlled with oil. The bed consisted of two sections of approx. 50 and 235 cm in length.

The first zone 50 cm in length contained catalyst from Example 1 98% diluted with untreated support material. The second zone 235 cm in length contained undiluted catalyst from Example 1.

The bed was flushed first with nitrogen, then with hydrogen and then heated within 5 hours to 240° C. in a stream of hydrogen of approx. 1528 Nl/h. Vaporisation of nitrobenzene in the stream of hydrogen was then begun. The nitrobenzene/hydrogen mixture arrived at the face of the catalyst bed at approx. 230° C. The specific loading of the catalyst was increased within 70 hours from 0.6 to 0.9 and, after a further 140 hours, to 1.06 kg/l×h, corresponding to a loading per unit area of 3081 kg/$m^2$×h, such that a mean loading of 1.04 kg/l×h was achieved. It was ensured that the catalyst did not become hotter than 440° C. at any point throughout the test.

After 140 hours, the oil temperature was raised from 240° C. to 300° C. The variation in oil temperature along the reaction tube was approx. ±1° C. The flow velocity of the oil along the tube surface was approx. 1.5 m/s.

The catalyst bed achieved a service life of approx. 1450 hours, after which the nitrobenzene content of the condensate rose from 0 to approx. 300 ppm, whereupon the catalyst had to be regenerated by burning off. Under the stated reaction conditions, the bed had thus achieved a productivity of approx. 1508 kg/l and is thus approx. 2.3 times more productive than the bed in Comparative Example 1 and approx. 30 times more productive than the bed in Comparative Example 2.

Mean selectivity was 99.3%.

Example 8

A 285 cm deep bed of catalysts produced according to Examples 5 and 1 was charged into a reaction tube of an internal diameter of approx. 26 mm and temperature-controlled with oil. The bed consisted of an intimate mixture of the catalysts, comprising 3% catalyst from Example 5 and 97% catalyst from Example 1.

The bed was flushed first with nitrogen, then with hydrogen and then heated within 5 hours to 240° C. in a stream of hydrogen of approx. 1528 Nl/h. Vaporisation of nitrobenzene in the stream of hydrogen was then begun. The nitrobenzene/hydrogen mixture arrived at the face of the catalyst bed at approx. 230° C. The specific loading of the catalyst was increased within 280 hours from 0.25 to 1.07, corresponding to a loading per unit area of 3110 kg/m²×h, such that a mean loading of 0.98 kg/l×h was achieved. It was ensured that the catalyst did not become hotter than 440° C. at any point throughout the test.

The oil temperature was raised in 20° C. stages after approx. 460, 1000 and 1100 hours from 240° C. to 300° C. The variation in oil temperature along the reaction tube was approx. ±1° C. The flow velocity of the oil along the tube surface was approx. 1.5 m/s.

The catalyst achieved a service life of approx. 1400 hours, after which the nitrobenzene content of the condensate rose from 0 to approx. 300 ppm, whereupon the catalyst had to be regenerated by burning off. Under the stated reaction conditions, the bed had thus achieved a productivity of approx. 1372 kg/l and is approx. 2 times more productive than the bed in Comparative Example 1 and approx. 27 times more productive than the bed in Comparative Example 2.

Mean selectivity was 99.0%.

Comparison between multi-tube reactor and Linde reactor.

Example 9 (Multi-tube reactor)

The test from Example 3 was repeated in a multi-tube reactor containing 55 tubes. The tubes had an internal diameter of approx. 26 mm, a wall thickness of approx. 2 mm and a length of approx. 3.5 m.

An approx. 285 cm deep catalyst bed was charged into each tubular reactor, giving a total of approx. 83 litres. The remainder of the bed consisted of inert packing. The total bed face area was approx. 292 cm².

Example 3 was repeated over 10 production cycles in this reactor. Regeneration was performed for 10 to 15 hours with $N_2$/air mixture and with pure air at a heat transfer medium temperature of 290 to 320° C. Mean selectivities were between 99.0 and 99.5%. The service lives for the individual production cycles are shown in Table 1.

Example 10 (Linde reactor)

The test from Example 3 was repeated in a multi-tube reactor containing 55 tubes. The tubes had an internal diameter of approx. 26 mm, a wall thickness of approx. 2 mm and a length of approx. 3.5 m. The reactor had an internal diameter of approx. 295 mm.

The catalyst bed of approx. 83 litres was placed to a depth of approx. 285 cm into the interstices between the tubes and had a face area of approx. 292 cm².

Wire mesh ring packing was placed above and below the catalyst bed. The cooling medium was passed through the tubes.

Example 3 was repeated over 10 production cycles in this reactor. Mean selectivities were between 99.1 and 99.4%.

The service lives for the individual production cycles are shown in Table 1.

TABLE 1

Service lives of the production cycles in Examples 9 and 10 in hours.

| Production cycle | Service life (Example 9) | Service life (Example 10) |
| --- | --- | --- |
| 1 | 1010 | 950 |
| 2 | 970 | 930 |
| 3 | 940 | 910 |
| 4 | 910 | 900 |
| 5 | 870 | 890 |
| 6 | 840 | 880 |
| 7 | 810 | 870 |
| 8 | 750 | 860 |
| 9 | 710 | 850 |
| 10 | 650 | 840 |

Although the invention has been described in detail in the foregoing for the purpose of illustration, it is to be understood that such detail is solely for that purpose and that variations can be made therein by those skilled in the art without departing from the spirit and scope of the invention.

What is claimed is:

1. A process for the production of aromatic amines by catalytic hydrogenation of corresponding aromatic nitro compounds in the gas phase on immobilised catalysts which contain a metal component comprising a metal selected from the group consisting of metals of VIIIa, Ib, IIb, IVa, Va, VIa, IVb and Vb groups of the periodic system of elements (Mendeleyev) on a ceramic support material having a BET surface area of less than 40 m²/g, at molar ratios of hydrogen to nitro group or nitro groups of 3:1 to 30:1 and temperatures in the catalyst bed of 180 to 500° C., wherein loading of the catalyst with the aromatic nitro compounds used is increased continuously or step-wise from 0.01–0.5 to 0.7–5.0 kg/l×h, wherein maximum loading is achieved within 10 to 1000 hours.

2. A process for the production of aromatic amines according to claim 1, wherein the process is performed in reactors in which the heat transfer medium is located within the tubes and the catalyst is arranged outside the tubes containing the heat transfer medium.

3. A process for the production of aromatic amines according to claim 1, wherein the catalyst used is a supported catalyst, in which palladium had been applied onto graphite or coke containing graphite as the support, which has a BET surface area of 0.05 to 10 m²/g, and the palladium content of which catalyst is 0.1 to 7 wt. %, relative to the weight of the catalyst, in combination with a catalyst which contains one or more metals comprising a component selected from the group consisting of VIIIa, Ib, IIb, IVa, Va, VIa, IVb and Vb groups on a ceramic support material having a BET surface area of less than 40 m²/g, and wherein the quantity ratio of graphite supported catalyst to ceramic supported catalyst is between 1/1 and 1/1000 parts by weight.

4. A process for the production of aromatic amines according to claim 1, wherein the catalyst beds are diluted with inert packing and optionally have activity gradients.

* * * * *